US010702603B2

(12) United States Patent
Conley et al.

(10) Patent No.: US 10,702,603 B2
(45) Date of Patent: *Jul. 7, 2020

(54) METHODS AND COMPOSITIONS FOR INACTIVATING ENVELOPED VIRUSES

(71) Applicant: Biogen MA Inc., Cambridge, MA (US)

(72) Inventors: Lynn Edward Conley, Raleigh, NC (US); Yinying Tao, Morrisville, NC (US)

(73) Assignee: Biogen MA Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/211,302

(22) Filed: Dec. 6, 2018

(65) Prior Publication Data

US 2019/0175738 A1 Jun. 13, 2019

Related U.S. Application Data

(63) Continuation of application No. 14/419,968, filed as application No. PCT/US2013/053781 on Aug. 6, 2013, now Pat. No. 10,188,732.

(60) Provisional application No. 61/680,039, filed on Aug. 6, 2012.

(51) Int. Cl.
| | |
|---|---|
| *A61K 38/00* | (2006.01) |
| *A61K 47/20* | (2006.01) |
| *A61K 9/00* | (2006.01) |
| *A61K 47/24* | (2006.01) |
| *C07K 14/705* | (2006.01) |
| *C12N 7/00* | (2006.01) |
| *A61K 47/18* | (2017.01) |
| *A61K 38/17* | (2006.01) |

(52) U.S. Cl.
CPC ............ *A61K 47/20* (2013.01); *A61K 9/0019* (2013.01); *A61K 38/1793* (2013.01); *A61K 47/186* (2013.01); *A61K 47/24* (2013.01); *C07K 14/70578* (2013.01); *C12N 7/00* (2013.01); *C07K 2319/30* (2013.01); *C12N 2710/16763* (2013.01); *C12N 2740/13063* (2013.01)

(58) Field of Classification Search
CPC .. A61K 47/20; A61K 9/0019; A61K 38/1793; A61K 47/186; A61K 47/24; C07K 14/70578; C12N 7/00
See application file for complete search history.

(56) References Cited

U.S. PATENT DOCUMENTS

| 10,188,732 B2 | 1/2019 | Conley et al. | |
|---|---|---|---|
| 2009/0304739 A1 | 12/2009 | Rappuoli et al. | |
| 2014/0328874 A1* | 11/2014 | Roth | ............... G01N 33/56983 424/204.1 |

FOREIGN PATENT DOCUMENTS

| DE | 242 716 A3 | 2/1987 |
|---|---|---|
| EP | 0 278 487 A2 | 8/1988 |
| EP | 0 433 225 A1 | 6/1991 |
| WO | WO 92/16201 A1 | 10/1992 |
| WO | WO 01/62240 A2 | 8/2001 |
| WO | WO 02/092139 A1 | 11/2002 |
| WO | WO 2005/065708 A2 | 7/2005 |
| WO | WO 2008/107473 A1 | 9/2008 |
| WO | WO 2012/082931 A1 | 6/2012 |

OTHER PUBLICATIONS

International Search Report and Written Opinion for Application No. PCT/US2013/053781 dated Feb. 19, 2014.
International Preliminary Report on Patentability for Application No. PCT/US2013/053781 dated Feb. 19, 2015.
Extended European Search Report for Application No. 18200752.6 dated Feb. 7, 2019.
Aranha, Current issues in assuring virological safety of pharmaceuticals. BioProcess International 2012; 10: 12-17.
Arnold et al., Phase separation in the isolation and purification of membrane proteins. BioTechniques. 2007;43 427-40.
Bertrand et al., The impact of temperature on the inactivation of enteric viruses in food and water: a review. J Appl Microbiol. Jun. 2012;112(6):1059-74. doi: 10.1111/j.1365-2672.2012.05267.x. Epub Mar. 20, 2012.
Boschetti et al., Stability of minute virus of mice against temperature and sodium hydroxide. Biologicals. Sep. 2003;31(3):181-5.
Bosley et al., A method of HIV-1 inactivation compatible with antibody-based depletion of abundant proteins from plasma. Proteomics Clin Appl. Jun. 2008;2(6):904-7. Doi: 10.1002/prca.200780086. Epub May 6, 2008.
Buss et al., Monoclonal antibody therapeutics: history and future. Curr Opin Pharmacol. Oct. 2012;12(5):615-22. doi: 10.1016/j.coph.2012.08.001. Epub Aug. 21, 2012.
Cameron et al., Virus clearance methods applied in bioprocessing operaitons: an overviewof selected inactivation and removal methods. Pharm Bioprocess. 2014; 2:75-83.
Chadd et al., Therapeutic antibody expression technology. Curr Opin Biotechnol. Apr. 2001;12(2):188-94.
Chang et al., Inactivation strategy for pseudorabies virus in milk for production of biopharmaceuticals. Jpn J Vet Res. Nov. 2010;58(3-4):179-83.
Chen et al., Biodegradation of octylphenol polyethoxylate surfactant Triton X-100 by selected microorganisms. Bioresour Technol. Sep. 2005;96(13):1483-91. Epub Jan. 20, 2005.
Conley et al., Evaluation of eco-friendly zwitterionic detergents for enveloped virus inactivation. Biotechnol Bioeng. Apr. 2017;114(4):813-820. doi: 10.1002/bit.26209. Epub Nov. 9, 2016.
Cuatrecasas, P., Isolation of the insulin receptor of liver and fat-cell membranes (detergent-solubilized-( 125 I)insulin-polyethylene glycol precipitation-sephadex). Proc Natl Acad Sci U S A. Feb. 1972;69(2):318-22.

(Continued)

*Primary Examiner* — Maryam Monshipouri
(74) *Attorney, Agent, or Firm* — Wolf, Greenfield & Sacks, P.C.

(57) ABSTRACT

Aspects of the invention provide therapeutic recombinant protein preparations and methods of preparing therapeutic recombinant protein, which methods include contacting recombinant protein preparations with zwitterionic detergent at or above critical micelle concentration of the detergent.

15 Claims, 2 Drawing Sheets

(56) References Cited

OTHER PUBLICATIONS

Dichtelmüller et al., Robustness of solvent/detergent treatment of plasma derivatives: a data collection from Plasma Protein Therapeutics Association member companies. Transfusion. Sep. 2009;49(9):1931-43. Doi: 10.1111/j.1537-2995.2009.02222.x. Epub May 20, 2009.

Ecker et al., The therapeutic monoclonal antibody market. MAbs. 2015;7(1):9-14. doi: 10.4161/19420862.2015.989042.

Ejima et al., Effects of acid exposure on the conformation, stability, and aggregation of monoclonal antibodies. Proteins. Mar. 1, 2007;66(4):954-62.

Farshid et al., The clearance of viruses and transmissible spongiform encephalopathy agents from biologicals. Curr Opin Biotechnol. Oct. 2005;16(5):561-7.

Garavito et al., Detergents as tools in membrane biochemistry. J Biol Chem. Aug. 31, 2001;276(35):32403-6. Epub Jun. 29, 2001.

Helenius et al., Solubilization of membranes by detergents. Biochim Biophys Acta. Mar. 25, 1975;415(1):29-79. Biologicals. Jun. 2002;30(2):153-62.

Henrikson et al., Understanding detergent effects on lipid membranes: a model study of lysolipids. Biophys J. May 19, 2010;98(10):2199-205. doi: 10.1016/j.bpj.2010.01.037.

Hermann, Non-ionic-cationic micellar properties of dimethyldodecylamine oxide. J Phys Chem. 1962;66(2) 295-300.

Hesse et al., Developments and improvements in the manufacturing of human therapeutics with mammalian cell cultures. Trends Biotechnol. Apr. 2000;18(4):173-80.

Horowitz et al., Solvent/detergent-treated plasma: a virus-inactivated substitute for fresh frozen plasma. Blood. Feb. 1, 1992;79(3):826-31.

Horowitz et al., Virus inactivation by solvent/detergent treatment and the manufacture of SD-plasma. Vox Sang. 1998;74 Suppl 1:203-6.

Kashino, Separation methods in the analysis of protein membrane complexes. J Chromatogr B Analyt Technol Biomed Life Sci. Nov. 25, 2003;797(1-2):191-216.

Kerr et al., Adventitious Viruses Detected in Biopharmaceutical Bulk Harvest Samples over a 10 Year Period. PDA J Pharm Sci Technol. Sep.-Oct. 2010;64(5):481-5.

Korneyeva et al., Enveloped virus inactivation by caprylate: a robust alternative to solvent-detergent treatment in plasma derived intermediates.

Koynova et al., Interactions of surfactants and fatty acids with lipids. Curr Opin in Colloid Interface Sci. 2001;6:277-86.

McCue et al., Enveloped virus inactivation using neutral arginine solutions and applications in therapeutic protein purification processes. Biotechnol Prog. Jan.-Feb. 2014;30(1):108-12. doi: 10.1002/btpr.1816. Epub Nov. 11, 2013.

Miesegaes et al., Monoclonal antibody capture and viral clearance by cation exchange chromatography. Biotechnol Bioeng. Aug. 2012;109(8):2048-58. doi: 10.1002/bit.24480. Epub Apr. 8, 2012.

Miesegaes et al., Proceedings of the 2009 Viral Clearance Symposium. Dev Biol (Basel). 2010;133:69-74.

Nelson et al., Development trends for human monoclonal antibody therapeutics. Nat Rev Drug Discov. Oct. 2010;9(10):767-74. doi: 10.1038/nrd3229. Epub Sep. 3, 2010.

Nimrod et al., Environmental estrogenic effects of alkylphenol ethoxylates. Crit Rev Toxicol. May 1996;26(3):335-64.

Ouellet et al., Purification and characterization of recombinant microsomal prostaglandin E synthase-1. Protein Expr Purif. Dec. 2002;26(3):489-95.

Privé, G., Detergents for the stabilization and crystallization of membrane proteins. Methods. Apr. 2007;41(4):388-97.

Remington, Fundamental strategies for viral clearance. BioProcess International 2015; 13 pp. 10-17.

Roberts et al., Virus inactivation in a factor VIII/VWF concentrate treated using a solvent/detergent procedure based on polysorbate 20. Biologicals. Jan. 2009;37(1):26-31. doi: 10.1016/j.biologicals.2008.08.003. Epub Oct. 10, 2008.

Roberts, Virus inactivation by solvent/detergent treatment using Triton X-100 in a high purity factor VIII. Biologicals. Sep. 2008;36(5):330-5. doi: 10.1016/j.biologicals.2008.06.002.

Russell-Harde et al., The use of Zwittergent 3-14 in the purification of recombinant human interferon-beta Ser17 (Betaseron). J Interferon Cytokine Res. Jan. 1995;15(1):31-7.

Schik, Effect of temperature on the critical micelle concentration of nonionic detergents. Thermodynamics of Micelle Formation. 1963;67(9): 1796-1799.

Shukla et al., Recent advances in large-scale production of monoclonal antibodies and related proteins. Trends Biotechnol. May 2010;28(5):253-61. doi: 10.1016/j.tibtech.2010.02.001. Epub Mar. 19, 2010.

Shukla et al., Viral clearance for biopharmaceutical downstream processes. Pharm Bioprocess. 2015;3:127-38.

Sofer, G., Inactivation of viruses. BioPharm International. 2003: S6-S7.

Tanford et al., Molecular characterization of proteins in detergent solutions. Biochemistry. May 21, 1974;13(11):2369-76.

Umbreit et al., Relation of detergent HLB number to solubilization and stabilization of D-alanine carboxypeptidase from Bacillus subtilis membranes. Proc Natl Acad Sci U S A. Oct. 1973;70(10):2997-3001.

Utz, Studies on the inactivation of influenza and Newcastle disease viruses by a specific lipid fraction of normal animal sera. J Immunol. Nov. 1949;63(3):273-9.

Walsh, Biopharmaceutical benchmarks. Nat Biotechnol. Oct. 2014;32(10):992-1000. doi: 10.1038/nbt.3040.

Welling-Wester et al., Detergent extraction of herpes simplex virus type 1 glycoprotein D by zwitterionic and non-ionic detergents and purification by ion-exchange high-performance liquid chromatography. J Chromatogr A. Aug. 7, 1998;816(1):29-37.

Westoby et al., Effects of solution environment on mammalian cell fermentation broth properties: enhanced impurity removal and clarification performance. Biotechnol Bioeng. Jan. 2011;108(1):50-8. doi: 10.1002/bit.22923.

Xie et al., An improved procedure for the purification of catalytically active alkane hydroxylase from Pseudomonas putida GPo1. Appl Biochem Biotechnol. Oct. 2011;165(3-4):823-31. doi: 10.1007/s12010-011-9300-5. Epub Jun. 7, 2011.

Zhou, Process scale purification of antibodies. John Wiley and Sons, Inc., 2009; 169-86 Orthogonal Virus Clearance Applications in Monoclonal Antibody Production.

\* cited by examiner

METHODS AND COMPOSITIONS FOR INACTIVATING ENVELOPED VIRUSES

RELATED APPLICATIONS

This application is a continuation application of U.S. patent application Ser. No. 14/419,968, filed Feb. 6, 2015, now U.S. Pat. No. 10,188,732 issued Jan. 29, 2019, which is a national stage filing under 35 U.S.C. § 371 of international application number PCT/US2013/053781, filed Aug. 6, 2013, which was published under PCT Article 21(2) in English and claims the benefit under 35 U.S.C. § 119(e) of U.S. provisional application No. 61/680,039, filed Aug. 6, 2012, each of which is incorporated by reference herein in its entirety.

FIELD OF THE INVENTION

Aspects and embodiments of the invention relate to the field of therapeutic protein production technologies.

BACKGROUND

Biopharmaceutical agents such as therapeutic recombinant proteins are often produced using rodent cells, insect cells, or mammalian cells. A concern associated with the production of biopharmaceuticals in this manner is potential viral contamination resulting from viral infection of the cells. One way to alleviate this concern is to inactivate the viruses.

SUMMARY OF THE INVENTION

Treatment of cells with non-ionic detergent is generally an effective method for inactivating enveloped virus such as, for example, murine leukemia virus (MuLV) present in Chinese Hamster Ovary (CHO) cells. The lipid-containing virus envelope, which is required for attachment of the virus to a host cell, is disrupted by reaction with detergent. As a result, the virus is prevented from attaching to and entering a host cell. Classical solvent/detergent (SD) viral inactivation systems employ organic solvents such as tri-n-butyl phosphate (TnBP) and non-ionic detergents such as Polysorbate 80 or TRITON® X-100, which not only adversely affect the protein production process, but also pose economic and wastewater concerns in some countries because of the ecotoxic nature of the components.

The present invention provides, inter alia, methods of preparing recombinant proteins, which methods utilize eco-friendly, cost-effective, non-protein denaturing zwitterionic detergents for viral inactivation. The invention is based in part on the surprising discovery that zwitterionic detergent used at or above its critical micelle concentration (CMC), generally in the absence of solvent, effectively inactivates enveloped virus(es) without adversely affecting biological activity of, for example, therapeutic proteins (e.g., recombinant proteins).

Thus, in various aspects of the invention, provided herein are methods of preparing a protein such as a recombinant protein (e.g., therapeutic recombinant protein), the methods comprising (or consisting of, or consisting essentially of) contacting a protein preparation with a zwitterionic detergent in an amount sufficient to inactivate enveloped virus, wherein the amount is at a concentration above critical micelle concentration of the detergent and does not inhibit biological activity of the protein. As used herein, "contacting" may refer to causing any two or more components to come into contact. It is to be understood that any protein described herein may be a therapeutic protein such as, for example, a therapeutic recombinant protein (e.g., antibody). Thus, any methods of preparing protein, as described herein, may also be used to prepare a recombinant protein and vice versa. Non-limiting examples of proteins/recombinant proteins according to the various aspects and embodiments of the invention are described elsewhere herein.

In some embodiments, the methods further comprise culturing in cell culture media cells that express the protein. In some embodiments, the methods further comprise purifying the protein. In some embodiments, the protein preparation is contacted with the zwitterionic detergent during the culturing step and/or after the culturing step and/or during the purifying step (e.g., at any of the purification steps when there are multiple purification steps).

In some embodiments, the concentration above the critical micelle concentration is about 2 times (2×) to about 10× the critical micelle concentration of the zwitterionic detergent. In some embodiments, the concentration above the critical micelle concentration is 1.5×, 2×, 2.5×, 3×, 3.5×, 4×, 4.5×, 5×, 5.5×, 6×, 6.5×, 7×, 7.5×, 8×, 8.5×, 9×, 9.5×, or 10× the critical micelle concentration zwitterionic detergent, or higher. In some embodiments, the critical micelle concentration of the zwitterionic detergent is less than 50×, or less than about 50× the critical micelle concentration of the zwitterionic detergent.

In some embodiments, greater than about 4 log ($>10^4$) inactivation of enveloped virus is achieved. In some embodiments, greater than 4 log, 5 log, 6 log, 7 log, 8 log, 9 log, or 10 log inactivation of enveloped virus is achieved. In some embodiments, the greater than 4 log, 5 log, 6 log, 7 log, 8 log, 9 log, or 10 log inactivation of enveloped virus is achieved within about 30 minutes to about 2 hours of contacting the protein preparation with zwitterionic detergent. In some embodiments, greater than 4 log, or greater than about 4 log, inactivation of enveloped virus is achieved within less than 1 hour (e.g., about 45 min) of contacting the protein preparation with zwitterionic detergent.

In some embodiments, the protein is recombinant protein. In such embodiments, the recombinant protein may be or may comprise tumor necrosis factor (TNF) inhibitor. In some embodiments, the TNF inhibitor is etanercept. It should be appreciated that other recombinant proteins can be prepared using the methods described herein.

In some embodiments, the enveloped virus is associated with a rodent cell line. In some embodiments, the enveloped virus is Xenotropic Murine Leukemia Virus (XMuLV). In some embodiments, the enveloped virus is Suid Herpesvirus 1 (SuHV-1). In some embodiments, the enveloped virus is associated with a mammalian cell line.

In some embodiments, the zwitterionic detergent is not classified as ecotoxic, or is considered ecofriendly.

In some embodiments, the zwitterionic detergent is N,N-dimethyldodecylamine N-oxide (LDAO), N-dodecyl-N,N-dimethyl-3-ammonio-1-propanesulfonate (sulfobetaine 3-12), N-tetradecyl-N,N-dimethyl-3-ammonio-1-propanesulfonate (sulfobetaine 3-14), or N-hexadecyl-N,N-dimethyl-3-ammonio-1-propanesulfonate (sulfobetaine 3-16). In some embodiments, the zwitterionic detergent is LDAO. LDAO is also known as dodecyl(dimethyl)amine oxide (DDAO).

In some embodiments, the methods do not comprise contacting the recombinant protein preparation with solvent. In some embodiments, the organic solvent tri-n-butyl phosphate (TnBP) is excluded from methods according to various aspects of the invention. Thus, according to some embodiments of the invention, provided herein are methods of preparing a protein, the methods comprising (or consisting of, or consisting essentially of) contacting a protein preparation with zwitterionic detergent in an amount sufficient to inactivate enveloped virus, wherein the amount is at a concentration above critical micelle concentration of the detergent and does not inhibit biological activity of the protein, and wherein the method does not comprise contacting the protein preparation with an organic solvent such as, for example, TnBP.

It should be appreciated that in some embodiments a combination of two or more zwitterionic detergents may be used.

In some aspects, the invention provides methods of preparing a recombinant protein, the methods comprising (or consisting of, or consisting essentially of) contacting a recombinant protein preparation with N,N-dimethyldodecylamine N-oxide (LDAO) in an amount sufficient to inactivate an enveloped virus, wherein the amount is at a concentration of about 2× to about 10× the critical micelle concentration of the detergent and does not inhibit biological activity of the recombinant protein. In some embodiments, the recombinant protein is or comprises tumor necrosis factor (TNF) inhibitor. In some embodiments, the TNF inhibitor is etanercept.

In various other aspects, the invention provides compositions, comprising (or consisting of, or consisting essentially of): (a) a biologically active recombinant protein; and (b) a zwitterionic detergent in an amount sufficient to inactivate enveloped virus, wherein the amount is at a concentration above critical micelle concentration of the detergent and does not inhibit biological activity of the recombinant protein. In some embodiments, the compositions comprise cell culture media.

In some embodiments, the concentration above the critical micelle concentration is about 2 times (2×) to about 10× the critical micelle concentration of the zwitterionic detergent. In some embodiments, the concentration above the critical micelle concentration is 1.5×, 2×, 2.5×, 3×, 3.5×, 4×, 4.5×, 5×, 5.5×, 6×, 6.5×, 7×, 7.5×, 8×, 8.5×, 9×, 9.5×, or 10× the critical micelle concentration zwitterionic detergent, or higher. In some embodiments, the critical micelle concentration of the zwitterionic detergent is less than 50×, or less than about 50× the critical micelle concentration of the zwitterionic detergent.

In some embodiments, greater than about 4 log (>$10^4$) inactivation of enveloped virus is achieved. In some embodiments, greater than 2 log, 3 log, 4 log, 5 log, 6 log, 7 log, 8 log, 9 log, or 10 log inactivation of enveloped virus is achieved. In some embodiments, the greater than 2 log, 3 log, 4 log, 5 log, 6 log, 7 log, 8 log, 9 log, or 10 log inactivation of enveloped virus is achieved within about 30 minutes to about 2 hours of contacting the protein preparation with zwitterionic detergent. In some embodiments, greater than 4 log, or greater than about 4 log, inactivation of enveloped virus is achieved within less than 1 hour (e.g., about 45 min) of contacting the protein preparation with zwitterionic detergent.

In some embodiments, the protein is a recombinant protein. In such embodiments, the recombinant protein may be or may comprise tumor necrosis factor (TNF) inhibitor. In some embodiments, the TNF inhibitor is etanercept. It should be appreciated that other recombinant proteins can be present in the compositions provided herein.

In some embodiments, the enveloped virus is associated with a rodent cell line. In some embodiments, the enveloped virus is Xenotropic Murine Leukemia Virus (XMuLV). In some embodiments, the enveloped virus is Suid Herpesvirus 1 (SuHV-1). In some embodiments, the enveloped virus is associated with a mammalian cell line.

In some embodiments, the zwitterionic detergent is not classified as ecotoxic, or is considered ecofriendly.

In some embodiments, the zwitterionic detergent is N,N-dimethyldodecylamine N-oxide (LDAO), N-dodecyl-N,N-dimethyl-3-ammonio-1-propanesulfonate (sulfobetaine 3-12), N-tetradecyl-N,N-dimethyl-3-ammonio-1-propanesulfonate (sulfobetaine 3-14), or N-hexadecyl-N,N-dimethyl-3-ammonio-1-propanesulfonate (sulfobetaine 3-16). In some embodiments, the zwitterionic detergent is LDAO. LDAO is also known as dodecyl(dimethyl)amine oxide (DDAO).

In some embodiments, the compositions do not comprise solvent. In some embodiments, the organic solvent tri-n-butyl phosphate (TnBP) is excluded from a composition according to various aspects of the invention. Thus, according to some embodiments of the invention, provided herein are compositions comprising (or consisting of, or consisting essentially of): (a) a biologically active recombinant protein; and (b) a zwitterionic detergent in an amount sufficient to inactivate enveloped virus, wherein the amount is at a concentration above critical micelle concentration of the detergent and does not inhibit biological activity of the recombinant protein, and wherein the composition does not contain (i.e., is free of) organic solvent such as, for example, TnBP. In some embodiments, such compositions comprise cell culture media.

In some aspects of the invention, provided herein are compositions, comprising (or consisting of, or consisting essentially of): (a) a TNF inhibitor; and (b) a zwitterionic detergent that is N,N-dimethyldodecylamine N-oxide (LDAO), N-dodecyl-N,N-dimethyl-3-ammonio-1-propanesulfonate (sulfobetaine 3-12), N-tetradecyl-N,N-dimethyl-3-ammonio-1-propanesulfonate (sulfobetaine 3-14), or N-hexadecyl-N,N-dimethyl-3-ammonio-1-propanesulfonate (sulfobetaine 3-16) at a concentration of about 2× to about 10× the critical micelle concentration of the detergent. In some embodiments, the amount of the zwitterionic detergent is at a concentration that is sufficient to inactivate an enveloped virus without inhibiting biological activity of the recombinant protein. In some embodiments, the compositions comprise (a) etanercept; and (b) N,N-dimethyldodecylamine N-oxide (LDAO). In some embodiments, the compositions comprise cell culture media. In some embodiments, the compositions do not contain organic solvent.

Also provided herein, in some aspects of the invention, are compositions, comprising: (a) a recombinant protein (e.g., a purified recombinant protein, for example, purified tumor necrosis factor (TNF) inhibitor protein); and (b) a zwitterionic detergent in an amount of less than 0.05% of the composition. In some embodiments, the TNF inhibitor is etanercept. In some embodiments, the zwitterionic detergent is LDAO. In some embodiments, the compositions do not contain organic solvent.

Further provided herein, in some aspects, are methods of preparing a recombinant protein, the methods comprising contacting a recombinant TNF inhibitor protein preparation with N,N-dimethyldodecylamine N-oxide (LDAO) in an amount between 0.01% and 0.20% weight/volume (w/v) of the preparation. In some embodiments, the amount of LDAO is in an amount between 0.05% and 0.15% w/v of the preparation. In some embodiments, the recombinant TNF inhibitor protein preparation does not contain a solvent.

DETAILED DESCRIPTION OF THE INVENTION

Figure 1:
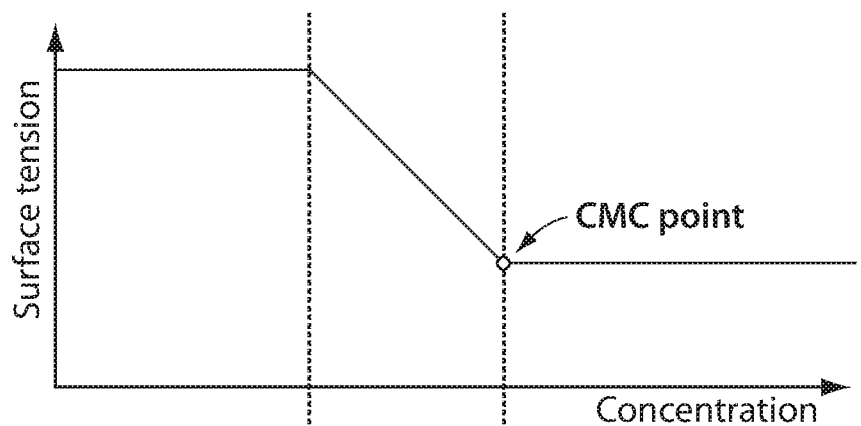
FIG. 1 shows a graph of surface tension versus log of concentration of detergent added. The arrow points to the critical micelle concentration (CMC) point.

Various aspects and embodiments of the invention contemplate contacting a protein preparation such as, for example, a recombinant protein preparation with zwitterionic detergent as an effective method for inactivating an enveloped virus. By so doing, the lipid-containing virus envelope is disrupted by interaction with the detergent, and the virus is not able to attach to and enter (e.g., infect) host cells. The methods described herein are particularly advantageous for preparing therapeutic recombinant proteins that are administered to subjects, for example, humans. By contacting a recombinant protein preparation with a zwitterionic detergent, according to the many aspects and embodiments of the invention, potentially dangerous enveloped virus(es) can be inactivated. The use of zwitterionic detergents, in particular, provides an advantage over existing methods because many such detergents are non-toxic, low cost and do not denature protein. Surprisingly, these ecofriendly detergents are effective as viral inactivation agents at concentrations much lower than that of other detergents used in classical solvent/detergent (SD) viral inactivation systems.

Thus, provided herein are methods of preparing a therapeutic protein (e.g., therapeutic recombinant protein such as antibody, antigen, hormone, enzyme), and compositions comprising a therapeutic protein. In various aspects and embodiments, methods according to the invention include contacting a recombinant protein preparation with a zwitterionic detergent. In some embodiments, the amount of the detergent is sufficient to inactivate an enveloped virus. In some embodiments, the amount of the detergent sufficient to inactivate the enveloped virus is a concentration above critical micelle concentration (CMC) of the detergent. In some embodiments, the concentration of the zwitterionic detergent does not inhibit biological activity of the recombinant protein.

One non-limiting example of a method according to the invention is as follows: (a) culture cells that express a recombinant protein in cell culture media at a temperature of about 7° C. to produce a recombinant protein preparation; (b) cool the recombinant protein preparation to ambient temperature (~25° C.), and adjust the pH of the preparation to about 5; (c) contact the recombinant protein preparation with zwitterionic detergent at a concentration that is above the critical micelle concentration of the detergent and is sufficient to inactivate enveloped virus; and (d) purify the recombinant protein.

Another non-limiting example of a method according to the invention is as follows: (a) culture cells that express recombinant protein in cell culture media at a temperature of about 37° C. to produce a recombinant protein preparation; (b) cool the recombinant protein preparation to ambient temperature (~25° C.) and adjust the pH of the preparation to about 5; (c) purify the recombinant protein; and (d) during the purification process (e.g., before or after any of the multiple purification steps), contact the recombinant protein preparation with a zwitterionic detergent at a concentration that is above the critical micelle concentration of the detergent and is sufficient to inactivate enveloped virus; and (e) remove the zwitterionic detergent (e.g., during a final purification step).

As used herein, a protein "preparation" or a recombinant protein "preparation" refers to a composition (typically liquid) containing a non-recombinant protein or a recombinant protein, respectively. A preparation may contain other components such as, for example, conditioned cell culture media (CCM). Conditioned CCM is media in which cells have been cultured for a period of time. Methods of preparing a recombinant protein, according to some embodiments of the invention, comprise contacting a recombinant protein preparation with a zwitterionic detergent in an amount sufficient to inactivate enveloped virus and that does not inhibit biological activity of the recombinant protein. In such embodiments, it is to be understood that the recombinant protein preparation contains the recombinant protein that is being prepared by the method (e.g., the recombinant protein of interest, for example, a tumor necrosis factor inhibitor such as etanercept). Various aspects and embodiments of the invention are directed to recombinant proteins; however, proteins that are not recombinant are also encompassed by each aspect and embodiment of the invention.

It is to be understood that the invention contemplates contacting the recombinant protein preparation with a zwitterionic detergent at any step of the recombinant protein preparation/production process, including at any step of a protein purification process. Protein purification methods are described in more detail below and include without limitation affinity chromatography and tangential flow filtration. For example, for affinity chromatography, the recombinant protein preparation may be contacted with a zwitterionic detergent at any step of the affinity chromatography process, then optionally removed during a binding and elution step. As another example, for tangential flow filtration, the recombinant protein preparation may be contacted with zwitterionic detergent at any step of the tangential flow filtration process, and then optionally removed by ultrafiltration or diafiltration—for example, ultrafiltration and diafiltration can remove detergent if the recombinant protein preparation is diluted to below critical micelle concentration. Thus, the recombinant protein preparation may be contacted with zwitterionic detergent prior to diluting the recombinant protein preparation to below critical micelle concentration.

Zwitterionic Detergents

A zwitterionic molecule is a neutral molecule with a positive and a negative electrical charge at different locations within the molecule. Zwitterionic detergents (e.g., detergents comprising zwitterionic molecules) may be used herein to solubilize biological macromolecules such as proteins present in viral envelopes. Examples of zwitterionic detergents that may be used according to various aspects and embodiments of the invention include without limitation 1-Dodecanoyl-sn-glycero-3-phosphocholine, 3-[(3-Cholamidopropyl)dimethylammonio]-1-propanesulfonate hydrate, 3-(4-tert-Butyl-1-pyridinio)-1-propanesulfonate, 3-(Benzyldimethylammonio)propanesulfonate, ASB-14 (amidosulfobetaine-14, 3-[N,N-Dimethyl(3-yristoylaminopropyl ammonio]propanesulfonate), ASB-14-4 (4-{N,N-Dimethyl-N-[3-(tetradecanoylamino)propyl] ammonio}butanesulfonate), ASB-16 (amidosulfobetaine-16), ASB-C80 (3-{N,N-Dimethyl-N-[3-(4-octylbenzoylamino)propyl]ammonio}propanesulfonate), ASB-C6Ø (4-n-Hexylbenzoylamido-propyl-dimethylammonio Sulfobetaine), ASB-C8Ø (4-n-octylbenzoylamidopropyl-dimethylammonio sulfobetaine), C7BzO (3-(4-Heptyl)phenyl-3-hydroxy-propyl-dimethylammonio-sulfobetaine), CHAPS (3-[(3-Cholamidopropyl) dimethylammonio]-1-propanesulfonate), CHAPSO (3-([3-Cholamidopropyl]dimethylammonio)-2-hydroxy-1-propanesulfonate), DDMAB, DDMAU, Dimethylethylammoniumpropane sulfonate, DMPS (Sodium 2,3-dimercaptopropanesulfonate monohydrate), EMPIGEN®BB (N,N-Dimethyl-N-dodecylglycine betaine), L-α-Lysophosphatidylcholine, Miltefosine hydrate, LDAO (DDAO, N,N-Dimethyldodecylamine N-oxide), N-Dodecyl-N,N-dimethyl-3-ammonio-1-propanesulfonate, NDSB 211 (3-[Dimethyl-(2-hydroxyethyl) ammonio]-1-propanesulfonate), NDSB 221 (3-(1-Methylpiperidinio)-1-propanesulfonate), O-(Decylphosphoryl) choline, PMAL®-B-100, PMAL®-C8 {Poly(maleic anhydride-alt-1-decene), 3-(dimethylamino)-1-propylamine derivative}, PMAL®-C10{Poly(maleic anhydride-alt-1-dodecene), 3-(Dimethylamino)-1-propylamine derivative}, PMAL®-C12{Poly(maleic anhydride-alt-1-tetradecene), 3-(dimethylamino)-1-propylamine derivative}, sulfobetaine 3-8 (3-(N,N-Dimethyloctylammonio)propanesulfonate inner salt), sulfobetaine 3-10 (3-(Decyldimethylammonio) propanesulfonate inner salt), sulfobetaine 3-12 (N-Dodecyl-N,N-dimethyl-3-ammonio-1-propanesulfonate), sulfobetaine 3-14 (3-(N,N-Dimethylmyristylammonio) propanesulfonate), sulfobetaine 3-16 (3-(N,N-Dimethylpalmitylammonio)propanesulfonate), sulfobetaine 3-18 (3-(N,N-Dimethyloctadecylammonio)propanesulfonate), and surfactin. In some embodiments, LDAO, sulfobetaine 3-12, sulfobetaine 3-14, and/or sulfobetaine 3-16 are used to inactivate enveloped virus. In some embodiments, LDAO is used to inactivate enveloped virus.

Any of the zwitterionic detergents described herein may be used according to the invention at a concentration at or above critical micelle concentration (CMC) of the particular detergent being used. In some embodiments, the concentration above CMC is, or is about, 2 times (2×), 2.5×, 5× or 10× the CMC of the detergent. In some embodiments, the concentration of the detergent is not greater than 15×, 20× or 50× the CMC of the detergent. In some embodiments, the concentration of the detergent is less than 5× the CMC or less than 2× the CMC of the detergent. In some embodiments, the detergent used inactivate enveloped virus is at a concentration that is not greater than 2×, 5× or 10× the CMC of the detergent. In some embodiments, LDAO, sulfobetaine 3-12, sulfobetaine 3-14, and/or sulfobetaine 3-16 is/are used to inactivate enveloped virus at a concentration that is not greater than, or not greater than about 20× the CMC of LDAO, sulfobetaine 3-12, sulfobetaine 3-14, and/or sulfobetaine 3-16, respectively. In some embodiments, LDAO is used to inactivate enveloped virus at a concentration that is not greater than 10× the CMC of LDAO.

In some embodiments, the concentration of the detergent is about 0.01% to 0.2% weight/volume (w/v) of the recombinant protein preparation (e.g., 0.01%, 0.02%, 0.03%, 0.04%, 0.05%, 0.06%, 0.07%, 0.08. 0.09%, 0.10%, 0.11%, 0.12%, 0.13%, 0.14%, 0.15%, 0.16%, 0.17%, 0.18%, 0.19% or 0.20% w/v). In some embodiments, the concentration of the detergent is about 0.05% to about 0.15% w/v of the protein preparation.). In some embodiments, the concentration of the detergent is about (or is) 0.014% w/v of the recombinant protein preparation.

In various embodiments, zwitterionic detergents may be classified as Class B or Class C detergents according to the Wastewater Disposal Guidelines for Denmark, based on "ABC Classification" for organic chemicals discharged to a pubic wastewater treatment plant. The A, B, and C classes are as follows: A, detergent be eliminated/substituted due to potential irreversible human harm and/or high aquatic toxicity and detergent is non-degradable; B, concentration of the detergent must be within certain limits to insure that water quality criteria are observed; C, detergent can be discharged without concentration limits (includes detergents not classed A/B). In some embodiments, the zwitterionic detergent is classified as Class B or Class C. LDAO is classified as class C, whereas sulfobetaine detergents are classified as class B.

Critical Micelle Concentration

The critical micelle concentration (CMC) is understood in the art to refer to the concentration of detergent above which monomers self-assemble (e.g., spontaneously form) into non-covalent aggregates (Rosen M. Surfactants and Interfacial Phenomena. 3rd ed. 2004, Hoboken: John Wiley & Sons, Inc.; Helenius A. et al., Methods Enzymol, 1979, 56: 734-49; Mukerjee, P., Mysels K J, Critical Micelle Concentrations of Aqueous Surfactant Systems. Vol. NSRDS-NBS 36. 1970, Washington, D.C.: National Bureau of Standards). The CMC may occur over a narrow concentration range. When the total detergent concentration is below the CMC, detergent monomers are free in bulk solution; however, as more detergent is added above the CMC, additional detergent monomers form micelles. At concentrations above the CMC, detergents form complexes with lipophilic proteins and can solubilize membrane protein. Below the CMC, detergents merely partition into membranes without solubilizing membrane proteins. The exact molecular weight of a detergent/molecule influences the CMC, and CMC can vary with ionic strength and temperature. For example, for ionic detergents the CMC can be reduced by increasing the ionic strength of the solution, but is relatively unaffected by temperature. For non-ionic and zwitterionic detergents the CMC is relatively unaffected by ionic strength, but can increase significantly with lower temperature (Schick M. J. J. Phys. Chem. 1963, 67(9): 1796-99; Qin X., et al. J. Phys. Chem. B 2011, 115: 1991-98). Several physical-chemical factors can also affect the CMC of a given detergent. Generally, the CMC decreases as the hydrophobicity of the detergent increases. Other properties that directly affect the CMC include the characteristics of the hydrophobic and hydrophilic groups and solution additives such as electrolytes.

Critical micelle concentration (CMC) can be determined by various techniques (Schick, 1963, Normand & Eisele, 1993), including surface tension measurements (Mittal K. L., *J Pharm Sci,* 1972, 61(8): 1334-5, incorporated herein by reference) and dye (e.g., anilino-1-naphthalene sulfonic acid) binding experiments (De Vendittis E. et al. *Anal Biochem,* 1981, 115: 278-286, incorporated herein by reference). Generally, the value of the CMC can be determined by characterizing changes in a particular physicochemical property (e.g., surface tension) of the detergent solution as the concentration of the detergent increases. For example, the CMC can be determined by collecting surface tension measurements at a series of different surfactant concentrations. A specific surface tension curve as a function of the concentration may be generated (FIG. 1). The CMC point is marked by an abrupt change in the linear decline of surface tension. Other methods with the use of Optimizer-blueBALLS™ from G-Biosciences are also commercially available and can be more convenient than the traditional dye solubilization method. The Optimizer blueBALLS™ are glass balls coated with a hydrophobic blue dye that behaves as a membrane protein. After adding the balls to a series of detergent solutions, the solubilization of the dye occurs in the solutions where micelles are formed. The quantity of dye in each solution is directly proportional to the number of micelles. As a result, the optical density plot indicating the blue dye concentration dissolved in the solutions is obtained, and the point of inflection on the plot of observed data versus detergent concentration corresponds to the CMC of that detergent.

Examples of zwitterionic detergents and their corresponding CMC are presented in Table 1.

damage and/or lyse the protein coat of a virus, without adversely affecting (e.g., inhibiting) biological activity of, for example, a therapeutic recombinant protein. In some embodiments, "an amount sufficient to inactivate an enveloped virus" refers to a zwitterionic detergent concentration that is about 2× to about 15× its critical micelle concentration (CMC). In some embodiments, "an amount sufficient to inactivate an enveloped virus" refers to a zwitterionic detergent concentration that is 1.5×, 2×, 2.5×, 3×, 2.5×, 4×, 4.5×, 5×, 5.5×, 6×, 6.5×, 7×, 7.5×, 8×, 8.5×, 9×, 9.5×, 10×, 10.5×,

TABLE 1

Examples of Zwitterionic Detergents and Corresponding CMC
Zwitterionic Detergents

| Detergent | Cat. No. | M.W. (anhydrous)* | CMC (mM)[b] | Aggregation No. | Average micellar weight | Size |
|---|---|---|---|---|---|---|
| 3-[N,N-Dimethyl(3-myristoylaminopropyl)ammonio] propanesulfonate, Amidosulfobetaine-14 (ASB-14) | 182750 | 434.7 | — | — | — | 5 g, 25 g |
| Amidosulfobetaine-16 (ASB-16) | 182775 | 462.7 | — | — | — | 5 g, 25 g |
| 3-[(3-cholamidopropyl)dimethylammonio]-1-propanesulfonate (CHAPS) | 220201 | 614.9 | 6-10 | 4-14 | 6,000 | 1 g<br>5 g<br>10 g<br>25 g |
| 3-([3-Cholamidopropyl]dimethylammonio)-2-hydroxy-1-propanesulfonate (CHAPSO) | 220202 | 630.9 | 8 | 11 | 7,000 | 1 g<br>5 g |
| N-Dodecyl-N,N-(dimethylammonio)butyrate (DDMAB) | 252000 | 299.5 | 4.3 | — | — | 5 g |
| N-Dodecyl-N,N-(dimethylammonio)undecanoate (DDMAU) | 252005 | 397.7 | 0.13 | — | — | 5 g |
| N,N-Dimethyl-N-dodecylglycine betaine, N-(Alkyl C10-C16)-N,N-dimethylglycine betaine (e.g., EMPIGEN BB ® Detergent, 30% Solution) | 324690 | 272.0 | 1.6-2.1 | — | — | 100 ml |
| Lauryldimethylamine Oxide (LDAO), 30% Solution | 428011 | 229.4 | 1-2 | 76 | 17,000 | 100 ml |
| n-Octyl-N,N-dimethyl-3-ammonio-1-propanesulfonate (e.g. ZWITTERGENT ® 3-08 Detergent) | 693019 | 279.6 | 330 | — | — | 5 g |
| n-Decyl-N,N-dimethyl-3-ammonio-1-propanesulfonate (e.g. ZWITTERGENT ® 3-10 Detergent) | 693021 | 307.6 | 25-40 | 41 | 12,500 | 5 g<br>25 g |
| n-Dodecyl-N,N-dimethyl-3-ammonio-1-propanesulfonate (e.g. ZWITTERGENT ® 3-12 Detergent) | 693015 | 335.6 | 2-4 | 55 | 18,500 | 5 g<br>25 g |
| n-Tetradecyl-N,N-dimethyl-3-ammonio-1-propanesulfonate (e.g. ZWITTERGENT ® 3-14 Detergent) | 693017 | 363.6 | 0.1-0.4 | 83 | 30,000 | 5 g<br>25 g<br>100 g |
| n-Hexadecyl-N,N-dimethyl-3-ammonio-1-propanesulfonate (e.g. ZWITTERGENT ® 3-16 Detergent) | 693023 | 391.6 | 0.01-0.06 | 155 | 60,000 | 5 g<br>25 g |

*Average molecular weights are given for detergents composed of mixtures of chain lengths
[b]Temperature 20-25° C.
EMPIGEN BB ® is a registered trademark of Allbright & Wilson.
Reprinted/modified from DETERGENTS: A guide to the properties and uses in biological systems (2001 by Calbiochem-Novabiochem Corporation).

As used herein, "an amount sufficient to inactivate an enveloped virus" with reference to a zwitterionic detergent may refer to an amount (e.g., concentration, volume, weight ratio) of detergent at or above critical micelle concentration of the detergent that is effective to solubilize at least a portion of membrane proteins forming a protein coat around enveloped viruses, thereby lysing the virus. In some embodiments, "an amount sufficient to inactivate an enveloped virus" is an amount of zwitterionic detergent that will 11×, 11.5×, 12×, 12.5×, 13×, 13.5×, 14×, 14.5×, or 15× CMC. In some embodiments, "an amount sufficient to inactivate an enveloped virus" refers to a zwitterionic detergent concentration that is 2.5× or 5× CMC.

As used herein, the biological activity of a recombinant protein is not considered to be inhibited if the recombinant protein retains greater than 98%, greater than 95%, greater than 90%, greater than 85%, greater than 80%, greater than 75%, greater than 70%, greater than 65%, greater than 60%, greater than 55%, or greater than 50% biological activity after contact with zwitterionic detergent. In some embodiments, the biological activity of a recombinant protein is not inhibited if the recombinant protein retains greater than about 98% (or greater than 98%) or greater than about 95% (or greater than 95%) biological activity after contact with zwitterionic detergent. Protein activity assays are well-known in the art, the conditions of which may depend on the particular recombinant protein. Any protein activity assay can be used with any of the aspects and/or embodiments described herein.

In various aspects and embodiments of the invention, the methods and compositions do not contain a solvent, for example, an organic solvent or an inorganic solvent. In some embodiments, the methods and compositions do not contain tri-n-butyl phosphate (TnBP).

Enveloped Viruses

Many viruses have viral envelopes covering their protein capsids. The envelopes typically are derived from portions of the host cell membranes (phospholipids and proteins), but include some viral glycoproteins. Functionally, viral envelopes are used to help viruses enter host cells. Glycoproteins on the surface of the envelope serve to identify and bind to receptor sites on the host's membrane. The viral envelope then fuses with the host's membrane, allowing the capsid and viral genome to enter and infect the host. The lipid bilayer envelope of viruses is relatively sensitive to detergents. Provided herein in various aspects and embodiments of the invention are zwitterionic detergents that inactivate enveloped viruses by damaging, and in some embodiments, lysing the viral envelope. The enveloped viruses described herein can be classified as DNA (single-stranded or double-stranded), RNA, or reverse transcribing viruses. Examples of enveloped viruses include without limitation Herpesviridae (e.g., Herpes simplex virus, varicella-zoster virus, cytomegalovirus, Epstein-Barr virus), Hepadnaviridae (e.g., Hepatitis B virus), Togaviridae (e.g., Rubella virus), Arenaviridae (e.g., Lymphocytic choriomeningitis virus), Flaviviridae (e.g., Dengue virus, Hepatitis C virus, Yellow fever virus), Orthomyxoviridae (e.g., Influenzavirus A, Influenzavirus B, Influenzavirus C, Isavirus, Thogotovirus), Paramyxoviridae (e.g., Measles virus, Mumps virus, Respiratory syncytial virus, Rinderpest virus, Canine distemper virus), Bunyaviridae (e.g., California encephalitis virus, Hantavirus), Filoviridae (e.g., Ebola virus, Marburg virus), Coronaviridae (e.g., Corona virus), Astroviridae (e.g., Astrovirus), Bornaviridae (e.g., Borna disease virus), and Arteriviridae (e.g., Arterivirus, Equine Arteritis Virus).

In some embodiments, the preparation of recombinant protein includes the use of single-cell suspension cultures in stirred-tank bioreactors of variable sizes (Wurm F. M. (2004) Nat. Biotechnol. 22, 1393-98; Kretzmer G. (2002) Appl. Microbiol. Biotechnol. 59, 135-42; Chu L. et al. (2001) Curr. Opin. Biotechnol. 12, 180-87, incorporated herein by reference). The cells may be maintained in media that is optimized for suspension growth at high cell density, for example, in the absence of serum and/or other animal-derived components. In some embodiments, cells may be cultured during the entire protein production phase without the addition of nutrient additives (batch culture). In some embodiments, nutrients may be periodically added to the culture to prolong cell viability and protein production (extended- or fed-batch culture). In some instances, reducing the temperature to 30° C. to 33° C., increasing osmolarity, or adding histone deacetylase inhibitors such as sodium butyrate or valproic acid may enhance protein productivity in both batch and fed-batch processes. Such additional steps are contemplated herein.

Cells (including recombinant cells) according to the various aspects and embodiments invention include without limitation rodent cells (e.g., Chinese Hamster Ovary (CHO) cells), insect cells (e.g., *Spodoptera frugiperda* cells), and mammalian cells (e.g., Human Embryonic Kidney 293 (HEK293) cells).

Cells that express a recombinant protein may be cultured over a range of temperatures suitable for cell growth and replication, for example, between 4° C. and 42° C. In some embodiments, the cells are cultured at a temperature of about 37° C. In some embodiments, the cells are cultured at a temperature of about 30° C. to about 33° C. In some embodiments, after cells are cultured, the recombinant protein preparation (e.g., cells, CCM, and the recombinant protein) may be cooled to, for example, 4° C. before contacting the recombinant protein preparation with a zwitterionic detergent. The cells may be cultured for any length of time necessary to express/produce a recombinant protein at any desired concentration.

In some embodiments, after recombinant protein-expressing cells are cultured in cell culture media (CCM), the pH of the recombinant protein preparation is adjusted. The pH of the preparation may be adjusted to within a range of about pH 4.5 to about pH 7.5. In some embodiments, the pH of the recombinant protein preparation is adjusted to 4.5, 5.0, 5.5, 6.0, 6.5, 7.0 or 7.5. In some embodiments, the pH of the recombinant protein preparation is adjusted to pH 5, or to about pH 5. In some embodiments, the pH is adjusted to a pH at which the zwitterionic detergent is neutral.

In some embodiments, the recombinant protein is purified. Protein purification methods include without limitation extraction, precipitation and differential solubilization, ultracentrifugation, and chromatographic methods such as size exclusion chromatography, separation based on charge or hydrophobicity, ion exchange chromatography, affinity chromatography and high performance liquid chromatography (HPLC).

It should be understood that the recombinant protein preparation may be contacted with a zwitterionic detergent at any temperature, at any pH, for any suitable time, and under any suitable conditions (e.g., in the presence or absence of salt, buffers, etc.).

In some embodiments, the recombinant protein preparation may be contacted with a zwitterionic detergent at a temperature that is between about 4° C. and about 42° C. (e.g., 4° C., 5° C., 6° C., 7° C., 8° C., 9° C., 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., 31° C., 32° C., 33° C., 34° C., 35° C., 36° C., 37° C., 38° C., 39° C., 41° C., 41° C. or 42° C.). For example, in some embodiments, the recombinant protein preparation may be contacted with a zwitterionic detergent at a temperature of about 4° C. or about 25° C.

In some embodiments, the recombinant protein preparation may be contacted with a zwitterionic detergent at a pH of about pH 4.5 to about pH 7.5 (e.g., pH of 4.5, 5.0, 5.5, 6.0, 6.5, 7.0 or 7.5). For example, in some embodiments, the pH may be less than 4.5 or more than 7.5.

In some embodiments, the recombinant protein preparation may be contacted with a zwitterionic detergent for about 15 minutes (min) to about 48 hours (h), or more. For example, in some embodiments, the recombinant protein preparation may be contacted with a zwitterionic detergent for 15 min, 30 min, 45 min, 60 min, 2 h, 12 h, 18 h, 24 h, 36 h or 48 h.

Protein/Recombinant Protein Preparations

Protein preparations described herein may contain a (e.g., one or more) protein(s) such as, for example, recombinant protein(s). In various embodiments, the protein is a therapeutic recombinant protein. In some embodiments, the therapeutic recombinant protein replaces a protein that is deficient or abnormal (e.g., in the treatment of endocrine disorders, hemostasis, thrombosis, metabolic enzyme deficiency, pulmonary and gastrointestinal-tract disorders, immunodeficiencies), augments an existing biological pathway (e.g., hematopoiesis, fertility, immunoregulation), provides a novel function or activity (e.g., enzymatic degradation of macromolecules, enzymatic degradation of small-molecule metabolites, hemostasis, thrombosis), interferes with a molecules or organism (e.g., in cancer, immunoregulation, transplantation, pulmonary disorders, infectious disease, hemostasis and thrombosis, endocrine disorders), delivers other compounds or proteins, protects against a deleterious foreign agent, treats an autoimmune disease, treats cancer, or is used as a diagnostic tool.

Examples of therapeutic proteins for use with the various aspects and embodiments described herein include without limitation insulin (e.g., HUMULIN®, NOVOLIN®), insulin human inhalation (e.g., EXUBERA®), insulin aspart (e.g., NOVOLOG®), insulin glulisine (e.g., APIDRA®), insulin lispro (e.g., HUMALOG®), isophane insulin (e.g., NPH), insulin detemir (e.g., LEVEMIR®), insulin glargine (e.g., LANTUS®), insulin zinc extended (e.g., LENTE®, ULTRALENT®), pramlintide acetate (e.g., SYMLIN®), growth hormone (GH), somatotropin (e.g., GENOTROPIN® HUMATROPE®, NORDITROPIN®, NUTROPIN®, OMNITROPE®, PROTROPIN®, SIAZEN®, SEROSTIM®, VALTROPIN®), Mecasermin (e.g., INCRELEX®), Mecasermin rinfabate (e.g., IPlex), Factor VIII (e.g., BIOCLATE®, HELIXATE®, KOGENATE®, RECOMBINATE®, REFACTO®), Factor IX (e.g., BENEFIX®), Antithrombin III (e.g., THROMBATE III®), protein C concentrate (e.g., CEPROTIN®), β-Gluco-cerebrosidase (e.g., CEREZYME®), β-Gluco-cerebrosidase (e.g., CEREDASE® (purified from pooled human placenta), alglucosidase-χ, aronidase/χ-1-iduronidase (e.g., ALDURAZYME®), Idursulphase/Iduronate-2-sulphatase (e.g., ELAPRASE®), Galsulphase (e.g., NAGLAZYME®), Agalsidase-β/human χ-galactosidase A (e.g., FABRAZYME®), χ-1-Proteinase inhibitor (e.g., ARALAST®, PROLASTIN®), Lactase (e.g., LACTAID®), pancreatic enzymes (e.g., ARCO-LASE®, COTAZYM®, CREON®, DONNAZYME®, PANCREASE®, VIOKAS®E, ZYMASE®), Adenosine deaminase (e.g., ADAGEN®), pooled immunoglobulins (e.g., OCTAGAM®), Human albumin (e.g., ALBUMARC®, ALBUMIN®, ALBUMINAR®, ALBURX®, ALBUTEIN®, FLEXBUMIN®, BUMINATE®, PLASBUMIN®), erythropoietin, epoetin-χ (e.g., EPOGEN®, PROCRIT), darbepoetin-χ (e.g., ARANESP®), filrastim (e.g., NEUPOGEN®), pegfilgrastim (e.g., NEULASTA®), sargramostim (e.g., LEUKINE®), oprelvekin (e.g., NEUMEGA®), human follicle stimulating hormone (FSH) (e.g., GONAL-F®, FOLLISTIM®), human chorionic gonadotropin (e.g., OVIDREL®), lutopin-χ (e.g., LUVERIS®), type I alpha-interferon, interferon alfacon 1, consensus interferon (e.g., INFERGEN®), interferon-χ2a (IFN χ2a) (e.g., ROFERON-A®), PegInterferon-χ2a (e.g., PEGASYS®), Interferon-χ2b (IFN χ2b) (e.g., INTRO A®), PegInterferon-χ2b (PEG-INTRON®), Interfron-χ n3(IFN χ n3), alferon N, interferon-β1a(rIFN-β) (e.g., AVONEX®, REBIF®), interferon-β1b(rIFN-β) (e.g., BETASERON®), interferon-γ1b(IFN γ) (e.g., ACTIMMUNE®), aldesleukin (e.g., PROLEUKIN®), alteplase (e.g., ACTIVASE®), reteplase (e.g., RETAVASE®), tenecteplase (TNKase), urokinase (e.g., ABBOKINASE®), Factor VIIa (e.g., NOVOSEVEN®), drotrecogin-χ (e.g., XIGRIS®), salmon calcitonin (e.g., FORTICAL®, MIACALIN®), teriparatide (e.g., FORTEO®), exenatide (e.g., BYETTA®), octreotide (e.g., SANDOSTATIN)®, dibotermin-χ (e.g., INFUSE®), recombinant human bone morphogenic protein 7 (e.g., Osteogenic protein 1), histrelin acetate (e.g., SUPPRELIN® LA, VANTAS®), palifermin (e.g., KEPIVANCE®), becaplermin (e.g., REGRANEX®), trypsin (e.g., GRANULEX®), nesiritide (e.g., NATRECOR®), botulinum toxin type A (e.g., BOTOX®), botulinum toxin type B (e.g., MYOBLOCK®), collagenase (e.g., Collagenase, SANTYL®), human deoxyribonuclease I, dornase-χ (e.g., PULMOZYME®), hyaluronidase (e.g., AMPHADASE®), hyaluronidase (e.g., HYLENEX®), papin (e.g., ACCUZYME®, PANAFI®L), L-Asparaginase (e.g., ELSPAR®), peg-asparaginase (e.g., ONCASPAR®), rasburicase (e.g., ELITEK®), lepirudin (e.g., REFLUDAN®), bivalirudin (e.g., ANGIOMAX®), streptokinase (e.g., STREPTASE®), Anistreplase (e.g., EMINASE®), bevacizumab (e.g., AVASTIN®), cetuximab (e.g., ERBITUX®), panitumumab (e.g., VECTIBIX®), alemtuzumab (e.g., CAMPATH®), rituximab (e.g., RITUXAN®), trastuzumab (e.g., HERCEPTIN®), abatacept (e.g., ORENCIA®), anakinra (e.g., ANTRIL®, KINERET®), adalimumab (e.g., HUMIRA®), etanercept (e.g., ENBREL®), infliximab (e.g., REMICADE®), alefacept (e.g., AMEVIVE®), efalizumab (e.g., RAPTIVA®), natalizumab (e.g., TYSABRI®), eculizumab (e.g., SOLIRIS®), antithymocyte globulin (e.g., THYMOGLOBULIN®), basiliximab (e.g., SIMULECT®), daclizumab (e.g., ZENAPAX®), muromonab-CD3 (e.g., ORTHOCLONE®, OKT3), omalizumab (e.g., XOLAIR®), palivizumab (e.g., SYNAGIS®), enfuviritide (e.g., FUZEON®), abciximab (e.g., REOPRO®), pegvisomant (e.g., SOMAVERT®), crotalidae polyvalent immune Fab (e.g., CROFAB®), digoxin immune serum (e.g., DIGIFAB®), ranibizumab (e.g., LUCENTIS®), denileukin Diftitox (e.g., ONTAK®), ibritumomab tiuxetan (e.g., ZEVALIN®), gemtuzumab ozogamicin (e.g., MYLOTARG®), and tositumomab and I-tositumomab (e.g., BEXXAR®, BEXXAR® I-131).

In some embodiments, the therapeutic recombinant protein is a tumor necrosis factor (TNF) inhibitor. In some embodiments, the TNF inhibitor is etanercept.

Compositions

Provided herein are compositions that may comprise (a) a protein (e.g., recombinant protein) and (b) a zwitterionic detergent in an amount sufficient to inactivate enveloped virus and that does not inhibit biological activity of the protein. In some embodiments, the composition comprises cell culture media. In some embodiments, the composition does not comprise (i.e., is free of) solvent. Although, in some embodiments, the composition may comprise trace amounts of solvent. In some embodiments, the composition does not comprise tri-n-butyl phosphate (TnBP).

In one aspect, the invention provides a composition that comprises (a) recombinant protein and (b) zwitterionic detergent at a concentration above critical micelle concentration of the detergent, which concentration is sufficient to inactivate enveloped virus and does not inhibit biological activity of the recombinant protein. In some embodiments of this aspect, the composition comprises cell culture media. In some embodiments, the composition does not comprise solvent. In some embodiments, the composition does not comprise tri-n-butyl phosphate (TnBP).

In another aspect, the invention provides a composition that comprises (a) a recombinant protein, and (b) a zwitterionic detergent at a concentration of about 2 times (2×) to about 10× the critical micelle concentration of the detergent. In some embodiments of this aspect, the concentration is less than (or less than about) 50×, 40×, 30×, 20×, or 10× the critical micelle concentration. In some embodiments of this aspect, the concentration is less than about 10× the critical micelle concentration. In some embodiments of this aspect, the composition comprises cell culture media. In some embodiments, the composition does not comprise solvent. In some embodiments, the composition does not comprise tri-n-butyl phosphate (TnBP).

In yet another aspect, the invention provides compositions that comprise (a) a recombinant protein, and (b) a zwitterionic detergent at a concentration above critical micelle concentration of the detergent, which concentration is sufficient for greater than about 4 log (>10$^4$) inactivation of enveloped virus within 1 hour of contacting the zwitterionic detergent with the recombinant protein preparation enveloped virus and does not inhibit biological activity of the recombinant protein. In some embodiments of this aspect, the concentration of the zwitterionic detergent is sufficient to achieve greater than (or greater than about) 3 log, greater than 4 log, greater than 5 log, greater than 6 log, greater than 7 log, greater than 8 log, greater than 9 log, or greater than 10 log inactivation of enveloped virus within 1 hour of contacting the zwitterionic detergent with the recombinant protein preparation. In some embodiments of this aspect, the concentration of the zwitterionic detergent is sufficient to achieve greater than (or greater than about) 3 log, greater than 4 log, greater than 5 log, greater than 6 log, greater than 7 log, greater than 8 log, greater than 9 log, or greater than 10 log inactivation of enveloped virus within 2 hours of contacting the zwitterionic detergent with the recombinant protein preparation. In some embodiments of this aspect, the concentration of the zwitterionic detergent is sufficient to achieve greater than (or greater than about) 3 log, greater than 4 log, greater than 5 log, greater than 6 log, greater than 7 log, greater than 8 log, greater than 9 log, or greater than 10 log inactivation of enveloped virus within 3 hours of contacting the zwitterionic detergent with the recombinant protein preparation. In some embodiments of this aspect, the concentration of the zwitterionic detergent is sufficient to achieve greater than (or greater than about) 3 log, greater than 4 log, greater than 5 log, greater than 6 log, greater than 7 log, greater than 8 log, greater than 9 log, or greater than 10 log inactivation of enveloped virus within 4 hours of contacting the zwitterionic detergent with the recombinant protein preparation. In some embodiments of this aspect, the concentration of the zwitterionic detergent is sufficient to achieve greater than (or greater than about) 3 log, greater than 4 log, greater than 5 log, greater than 6 log, greater than 7 log, greater than 8 log, greater than 9 log, or greater than 10 log inactivation of enveloped virus within 5 hours of contacting the zwitterionic detergent with the recombinant protein preparation. In some embodiments of this aspect, the composition comprises cell culture media. In some embodiments, the composition does not comprise solvent. In some embodiments of this aspect, the composition does not comprise tri-n-butyl phosphate (TnBP).

In still another aspect, the invention provides a composition that comprises (a) cell culture media; (b) a recombinant tumor necrosis factor (TNF) inhibitor; and (c) a zwitterionic detergent at a concentration above critical micelle concentration of the detergent, which concentration is sufficient to inactivate enveloped virus and does not inhibit biological activity of the recombinant TNF inhibitor. In some embodiments of this aspect, the zwitterionic detergent is N,N-dimethyldodecylamine N-oxide (LDAO), N-dodecyl-N,N-dimethyl-3-ammonio-1-propanesulfonate (sulfobetaine 3-12), N-tetradecyl-N,N-dimethyl-3-ammonio-1-propanesulfonate (sulfobetaine 3-14), or N-hexadecyl-N,N-dimethyl-3-ammonio-1-propanesulfonate (sulfobetaine 3-16). In some embodiments of this aspect, the zwitterionic detergent is LDAO. In some embodiments of this aspect, the concentration of zwitterionic detergent that is sufficient to inactivate enveloped virus is about 2× (or 2×) to about 10× (or 10×) the critical micelle concentration of the zwitterionic detergent. In some embodiments of this aspect, the composition does not comprise a solvent. In some embodiments of this aspect, the composition does not comprise tri-n-butyl phosphate (TnBP).

In a further aspect, the invention provides a composition that comprises (a) cell culture media; (b) etanercept; and (c) a zwitterionic detergent at a concentration above critical micelle concentration of the detergent, which concentration is sufficient to inactivate enveloped virus and does not inhibit biological activity of the etanercept. In some embodiments of this aspect, the zwitterionic detergent is LDAO. In some embodiments of this aspect, the concentration of the zwitterionic detergent that is sufficient to inactivate enveloped virus is about 2× (or 2×) to about 10× (or 10×) the critical micelle concentration of the zwitterionic detergent. In some embodiments of this aspect, the composition does not comprise a solvent. In some embodiments, the composition does not comprise tri-n-butyl phosphate (TnBP).

In another aspect, the invention provides a composition that comprises (a) cell culture media; (b) a recombinant protein; and (c) a zwitterionic detergent that is N,N-dimethyldodecylamine N-oxide (LDAO), N-dodecyl-N,N-dimethyl-3-ammonio-1-propanesulfonate (sulfobetaine 3-12), N-tetradecyl-N,N-dimethyl-3-ammonio-1-propanesulfonate (sulfobetaine 3-14), or N-hexadecyl-N,N-dimethyl-3-ammonio-1-propanesulfonate (sulfobetaine 3-16) at a concentration above critical micelle concentration of the detergent, which concentration is sufficient to inactivate enveloped virus and does not inhibit biological activity of the recombinant protein. In some embodiments of this aspect, the biologically active recombinant protein is etanercept. In some embodiments of this aspect, the composition does not comprise a solvent. In some embodiments of this aspect, the composition does not comprise tri-n-butyl phosphate (TnBP).

In yet another aspect, the invention provides a composition that comprises (a) a recombinant protein, and (b) a zwitterionic detergent at a concentration above critical micelle concentration of the detergent, which concentration is sufficient to inactivate enveloped virus and does not inhibit biological activity of the recombinant protein, wherein the composition does not comprise solvent. In some embodiments of this aspect, the composition does not comprise tri-n-butyl phosphate (TnBP). In some embodiments, the composition comprises cell culture media.

Methods

Also provided herein are methods of preparing protein (e.g., recombinant protein). Methods may comprise contacting a protein preparation (e.g., recombinant protein preparation) with a zwitterionic detergent in an amount sufficient to inactivate enveloped virus, wherein the amount is at a concentration above critical micelle concentration of the detergent and does not inhibit biological activity of the protein.

In one aspect, the invention provides methods of preparing a recombinant protein, the methods comprising contacting a recombinant protein preparation with a zwitterionic detergent at a concentration above critical micelle concentration of the detergent, which concentration is sufficient to inactivate enveloped virus and does not inhibit biological activity of the recombinant protein. In some embodiments of this aspect, the method does not comprise contacting the protein preparation with solvent. In some embodiments of this aspect, the method does not comprise contacting the protein preparation with tri-n-butyl phosphate (TnBP).

In another aspect, the invention provides methods of preparing a recombinant protein, the methods comprising contacting a recombinant protein preparation with a zwitterionic detergent at a concentration of about 2 times (2×) to about 10× the critical micelle concentration of the detergent. In some embodiments of this aspect, the concentration is less than (or less than about) 50×, 40×, 30×, 20×, or 10× the critical micelle concentration. In some embodiments of this aspect, the concentration is less than 10× the critical micelle concentration. In some embodiments of this aspect, the method does not comprise contacting the protein preparation with solvent. In some embodiments of this aspect, the composition does comprise contacting the protein preparation with tri-n-butyl phosphate (TnBP).

In yet another aspect, the invention provides methods of preparing a recombinant protein, the methods comprising contacting a recombinant protein preparation with a zwitterionic detergent at a concentration above critical micelle concentration of the detergent, which concentration is sufficient for greater than about 4 log (>$10^4$) inactivation of enveloped virus within 1 hour of contacting the zwitterionic detergent with the recombinant protein preparation enveloped virus and does not inhibit biological activity of the recombinant protein. In some embodiments of this aspect, the concentration of the zwitterionic detergent is sufficient to achieve greater than (or greater than about) 3 log, greater than 4 log, greater than 5 log, greater than 6 log, greater than 7 log, greater than 8 log, greater than 9 log, or greater than 10 log inactivation of enveloped virus within 1 hour of contacting the zwitterionic detergent with the recombinant protein preparation. In some embodiments of this aspect, the concentration of the zwitterionic detergent is sufficient to achieve greater than (or greater than about) 3 log, greater than 4 log, greater than 5 log, greater than 6 log, greater than 7 log, greater than 8 log, greater than 9 log, or greater than 10 log inactivation of enveloped virus within 2 hours of contacting the zwitterionic detergent with the recombinant protein preparation. In some embodiments of this aspect, the concentration of the zwitterionic detergent is sufficient to achieve greater than (or greater than about) 3 log, greater than 4 log, greater than 5 log, greater than 6 log, greater than 7 log, greater than 8 log, greater than 9 log, or greater than 10 log inactivation of enveloped virus within 3 hours of contacting the zwitterionic detergent with the recombinant protein preparation. In some embodiments of this aspect, the concentration of the zwitterionic detergent is sufficient to achieve greater than (or greater than about) 3 log, greater than 4 log, greater than 5 log, greater than 6 log, greater than 7 log, greater than 8 log, greater than 9 log, or greater than 10 log inactivation of enveloped virus within 4 hours of contacting the zwitterionic detergent with the recombinant protein preparation. In some embodiments of this aspect, the concentration of the zwitterionic detergent is sufficient to achieve greater than (or greater than about) 3 log, greater than 4 log, greater than 5 log, greater than 6 log, greater than 7 log, greater than 8 log, greater than 9 log, or greater than 10 log inactivation of enveloped virus within 5 hours of contacting the zwitterionic detergent with the recombinant protein preparation. Calculating log inactivation of viruses is well known in the art. In some embodiments of this aspect, the methods do not comprise contacting the protein preparation with solvent. In some embodiments, the methods do not comprise contacting the protein preparation with tri-n-butyl phosphate (TnBP).

In still another aspect, the invention provides method of preparing recombinant tumor necrosis factor (TNF) inhibitor, the methods comprising contacting a recombinant protein preparation with a zwitterionic detergent at a concentration above critical micelle concentration of the detergent, which concentration is sufficient to inactivate enveloped virus and does not inhibit biological activity of the recombinant TNF inhibitor. In some embodiments of this aspect, the zwitterionic detergent is N,N-dimethyldodecylamine N-oxide (LDAO), N-dodecyl-N,N-dimethyl-3-ammonio-1-propanesulfonate (sulfobetaine 3-12), N-tetradecyl-N,N-dimethyl-3-ammonio-1-propanesulfonate (sulfobetaine 3-14), or N-hexadecyl-N,N-dimethyl-3-ammonio-1-propanesulfonate (sulfobetaine 3-16). In some embodiments of this aspect, the zwitterionic detergent is LDAO. In some embodiments of this aspect, the concentration of zwitterionic detergent that is sufficient to inactivate enveloped virus is about 2× (or is 2×) to about 10× (or is 10×) the critical micelle concentration of the zwitterionic detergent. In some embodiments of this aspect, the method does not comprise contacting the protein preparation with solvent. In some embodiments, the method does not comprise contacting the protein preparation with tri-n-butyl phosphate (TnBP).

In a further aspect, the invention provides methods of preparing etanercept, the methods comprising contacting an etanercept preparation with a zwitterionic detergent at a concentration above critical micelle concentration of the detergent, wherein the concentration is sufficient to inactivate enveloped virus and does not inhibit biological activity of the etanercept. In some embodiments of this aspect, the zwitterionic detergent is LDAO. In some embodiments of this aspect, the concentration of zwitterionic detergent that is sufficient to inactivate enveloped virus is about 2× (or is 2×) to about 10× (or is 10×) the critical micelle concentration of the zwitterionic detergent. In some embodiments of this aspect, the method does not comprise contacting the protein preparation with solvent. In some embodiments, the method does not comprise contacting the protein preparation with tri-n-butyl phosphate (TnBP).

In another aspect, the invention provides methods of preparing a recombinant protein, the methods comprising contacting a recombinant protein preparation with a zwitterionic detergent that is N,N-dimethyldodecylamine N-oxide (LDAO), N-dodecyl-N,N-dimethyl-3-ammonio-1-propanesulfonate (sulfobetaine 3-12), N-tetradecyl-N,N-dimethyl-3-ammonio-1-propanesulfonate (sulfobetaine 3-14), or N-hexadecyl-N,N-dimethyl-3-ammonio-1-propanesulfonate (sulfobetaine 3-16) at a concentration above critical micelle concentration of the detergent, which concentration is sufficient to inactivate enveloped virus and does not inhibit biological activity of the recombinant protein. In some embodiments of this aspect, the biologically active recombinant protein is etanercept. In some embodiments of this aspect, the method does not comprise contacting the protein preparation with solvent. In some embodiments, the method does not comprise contacting the protein preparation with tri-n-butyl phosphate (TnBP).

In yet another aspect, the invention provides methods of preparing a recombinant protein, the methods comprising contacting a recombinant protein preparation with a zwitterionic detergent at a concentration above critical micelle concentration of the detergent, wherein the concentration is sufficient to inactivate enveloped virus and does not inhibit biological activity of the recombinant protein, wherein the method does not comprise contacting the protein preparation with solvent. In some embodiments of this aspect, the method does not comprise contacting the protein preparation with tri-n-butyl phosphate (TnBP).

In any of the various aspects and embodiments of the invention, a recombinant protein preparation may contain a trace amount of a zwitterionic detergent. For example, in some instances, a recombinant protein preparation, even after being purified, may contain undetectable amounts of a zwitterionic detergent. In other embodiments, a recombinant protein preparation may contain about or less than 0.05%, about or less than 0.01%, about or less than 0.005%, or about or less than 0.001% of a zwitterionic detergent.

In particular embodiments, the zwitterionic detergent may be present in the recombinant protein preparation as a preservative, for example, to prevent or inhibit the growth of microorganisms. In such embodiments, the recombinant protein preparation may be contacted with a zwitterionic detergent before protein purification, during protein purification and/or after protein purification.

Kits

In various aspects of the invention, provided herein are kits comprising, consisting of, or consisting essentially of, any of the compositions described herein and one or more components packed in one or more containers (e.g., plastic or glass containers). Is some embodiments, the kit comprises a syringe or other means to deliver the composition to a subject (e.g., human). In some embodiments, the kit comprises instructions (or directions for obtaining instructions) for administering the composition to a subject.

Aspects and embodiments of the invention are further described below by way of non-limiting examples.

EXAMPLES

Example 1

A detergent below its critical micelle concentration (CMC) exists in a monomeric form and will bind to cell membranes. Once the detergent CMC is reached, the detergent self-assembles and forms micelles that will interact with the cell membrane and lyse the cell. Enveloped viruses contain lipid bilayer coats that can be lysed by detergents. Once the viral coat is lysed, the virus is unable to infect cells and therefore is inactivated. A study was performed with TRITON X-100® $(C_{14}H_{22}O(C_2H_4O)n)$ to confirm this theory. Viral inactivation studies were performed with TRITON X-100® at 1-2× CMC (0.02% w/w) at ambient temperature using 3 different antibodies. TRITON X-100® is a mixture with a range of molecular lengths, so the CMC has a range between 0.01-0.02% w/w at 25° C. in water. The results from this study confirmed the above theory and showed that >4 log of XMuLV inactivation was achieved within 45 min. Also confirmed during one of these viral inactivation studies was that below the CMC, the detergent was not effective at inactivating enveloped viruses. No viral inactivation was observed at 0.25-0.5× CMC (0.006% w/w).

The costs of the detergents described herein were evaluated to see if they could be used economically at the 15,000 liter cell culture scale. Most of the detergents used for solubilizing membrane proteins are produced for research purposes, and thus are expensive and cost prohibitive at the 15,000 liter scale.

The detergents were also evaluated to see how they would be classified under the wastewater Disposal Guidelines for Denmark. The guidelines for Denmark are based on the "ABC Classification" for organic chemicals discharged to a public wastewater treatment plant, as described above. Only Class B and C detergents were evaluated in viral clearance studies.

TRITON X-100 can be used together with solvent to prepare recombinant proteins; however, it is classified as a highly ecotoxic reagent in Denmark and requires special treatment for the waste disposal if used in a biological manufacturing process. As alternatives to harsh, ecotoxic detergent/solvent systems, five mild, ecofriendly detergents were identified and evaluated for viral inactivation effectiveness. The five detergents are shown in Table 2. These non-ionic and zwitterionic detergents meet current European (Danish) and US guidelines for discharge to a public wastewater treatment plant, are cost effective, are mild and are non-protein denaturing detergents that do not appear to impact protein bioactivity.

TABLE 2

Detergents evaluated during viral inactivation study

| Detergent | Detergent Type |
| --- | --- |
| Sulfobetaine-12 | Zwitterionic |
| Sulfobetaine-14 | Zwitterionic |
| Sulfobetaine-16 | Zwitterionic |
| Lauryldimethylaminoxide | Zwitterionic |
| Brij 35 | Non-Ionic |

Adverse effects of the detergents on product bioactivity were evaluated prior to initiation of the viral inactivation studies. The detergents were added individually to conditioned cell culture media (CCM) containing etanercept (referred to herein as recombinant protein preparation) and incubated at ambient temperature for 2 hours at 10× CMC of the detergent. Each recombinant protein preparation was purified over MABSELECT SURE™ and PHENYL SEPHAROSE® to reduce protein aggregates and misfolding. Ultrafiltration and diafiltration were performed using a formulation buffer. Purified recombinant protein was tested in a tumor necrosis factor (TNF) bioassay which showed that the biological activity of etanercept was retained when exposed to each of the five detergents.

A viral clearance study was then performed to assess the ability of each of the five detergents to inactivate Xenotropic Murine Leukemia Virus (XMuLV). The recombinant product, etanercept, is expressed in a well-characterized Chinese Hamster Ovary (CHO) cells which can harbor endogenous retrovirus or retrovirus-like particles. XMuLV represents a specific model having similar physical and chemical properties (same genus or family) to the suspected virus or virus like-particles present in the recombinant protein preparation. Suid herpesvirus-1 (SuHV-1) is also being used in viral clearance studies. SuHV-1 is considered a non-specific model virus—it is not an endogenous virus for a rodent cell line. Non-specific model viruses can be used to characterize robustness of the method for inactivating viruses. The characteristics of the nonspecific model virus(es) encompass a variety of physical and chemical properties such as: enveloped/non enveloped, size, chemical resistivity and genome (RNA/DNA). Per the International Conference on Harmonisation (ICH) Guidelines, when choosing nonspecific model viruses, preference should be given to viruses that display significant resistance to physical and/or chemical treatments. The data obtained from using such viruses provides useful information about the effectiveness of the methods described herein to remove and/or inactivate virus in general (see Table 3). SuHV-1, a large (120-200 nm) enveloped DNA virus with medium resistance to chemical treatments, was selected as the non-specific model to evaluate the effectiveness of LDAO and Sulflobetaine 3-16 to inactivate virus.

TABLE 3

Enveloped viruses used in viral clearance studies

| Virus Name | Size (nm) | Genome | Enveloped/Non-Enveloped | Chemical Resistivity |
|---|---|---|---|---|
| Xenotropic Murine leukemia virus | 80-110 | RNA | Enveloped | Low |
| Suid herpesvirus 1 | 120-200 | DNA | Enveloped | Medium |

Figure 2:
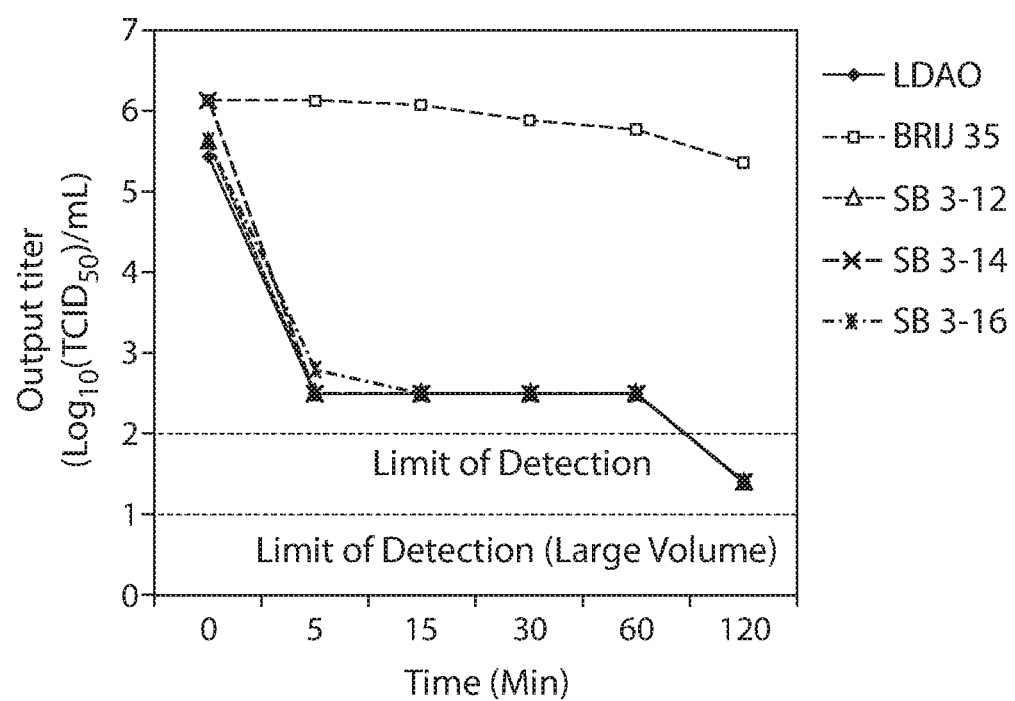
FIG. 2 show a graph of viral inactivation results after incubation with detergent for 120 minutes at room temperature.

Detergents at 10× CMC and XMuLV (5% V/V) were spiked into CCM for recombinant protein, etanercept, at room temperature. Samples were taken at various time points over a period of 120 minutes and measured for XMuLV infectivity. Four zwitterionic detergents inactivated >4 log XMuLV, while the non-ionic detergent, Brij-35 did not inactivate the virus. The results are shown in Table 4 and FIG. 2.

TABLE 4

Viral Inactivation results after incubation for 120 minutes at room temperature

| | Test % concentration (weight/volume) | Log Reduction Factor (120 min) |
|---|---|---|
| Sulfobetaine-12 | 1.3% | 4.2 |
| Sulfobetaine-14 | 0.14% | 4.7 |
| Sulfobetaine-16 | 0.024% | 4.2 |
| Lauryldimethylaminoxide | 0.46% | 4 |
| Brij-35 | 0.11% | <0.1 |

Additional XMuLV inactivation studies were performed for sulfobetaine-16 at 2.5× and 5× CMC, and for LDAO at 3× and 10× CMC at 4° C. (Table 5). The CMC value increases slightly as the temperature is lowered. The concentration of detergent may need to increase to disrupt the viral membrane coat and inactivate virus.

TABLE 5

Viral Inactivation results after incubation at 4° C.

| Virus | Detergent | Conc. (×CMC) | Time (min) | Log Reduction Factor (LRF) |
|---|---|---|---|---|
| X-MLV | LDAO | 10 | 15 | 3.07 |
| X-MLV | LDAO | 10 | 120 | 3.08 |
| X-MLV | LDAO | 3 | 120 | 3.14 |
| X-MLV | LDAO | 3 | 120 | 3.14 |
| X-MLV | SB 3-16 | 5 | 15 | 3.16 |
| X-MLV | SB 3-16 | 5 | 15 | 3.16 |

TABLE 5-continued

Viral Inactivation results after incubation at 4° C.

| Virus | Detergent | Conc. (×CMC) | Time (min) | Log Reduction Factor (LRF) |
|---|---|---|---|---|
| X-MLV | SB 3-16 | 2.5 | 120 | 3.15 |
| X-MLV | SB 3-16 | 2.5 | 120 | 3.14 |

Example 2

Additional XMuLV and SuHV-1 inactivation studies were performed for LDAO at 3× CMC for etanercept at 4° C., as described above in Example 1. Results are shown in Table 6.

TABLE 6

LDAO inactivation of etanercept.

| Virus | Concentration % (weight per volume) | Concentration X fold of CMC | Time Minutes | LRF |
|---|---|---|---|---|
| Run #1 | | | | |
| XuMLV | 0.14% | 3X | 5 | ≥2.88 |
| XuMLV | 0.14% | 3X | 15 | ≥2.88 |
| XuMLV | 0.14% | 3X | 30 | ≥2.88 |
| XuMLV | 0.14% | 3X | 60 | ≥2.88 |
| XuMLV | 0.14% | 3X | 120 | ≥4.72* |
| Run #2 | | | | |
| XuMLV | 0.14% | 3X | 5 | ≥2.83 |
| XuMLV | 0.14% | 3X | 15 | ≥2.83 |
| XuMLV | 0.14% | 3X | 30 | ≥2.83 |
| XuMLV | 0.14% | 3X | 60 | ≥2.83 |
| XuMLV | 0.14% | 3X | 120 | ≥4.67* |
| Run #3 | | | | |
| SuHV-1 | 0.14% | 3X | 5 | ≥5.39 |
| SuHV-1 | 0.14% | 3X | 15 | ≥5.09 |
| SuHV-1 | 0.14% | 3X | 30 | ≥5.09 |
| SuHV-1 | 0.14% | 3X | 60 | ≥5.09 |
| SuHV-1 | 0.14% | 3X | 120 | ≥6.46* |
| Run #4 | | | | |
| SuHV-1 | 0.14% | 3X | 5 | ≥5.09 |
| SuHV-1 | 0.14% | 3X | 15 | 4.79 |
| SuHV-1 | 0.14% | 3X | 30 | ≥5.09 |
| SuHV-1 | 0.14% | 3X | 60 | ≥5.09 |
| SuHV-1 | 0.14% | 3X | 120 | ≥6.51* |

Large volume sampling*.
Xenotrophic Murine Leukemia Virus = XuMLV
Suid Herpes-1 = SuHV-1.
Log reduction factor = LRF Example 3

Additional XMuLV and SuHV-1 inactivation studies were performed for LDAO at 3× CMC for a recombinant TNF inhibitor protein at 4° C., as described above in Example 1. Results are shown in Table 7.

TABLE 7

LDAO inactivation recombinant TNF inhibitor protein.

| Virus | Concentration % (weight per volume) | Concentration X fold of CMC | Time Minutes | LRF |
|---|---|---|---|---|
| Run #1 | | | | |
| XuMLV | 0.14% | 3X | 5 | ≥3.5 |
| XuMLV | 0.14% | 3X | 15 | ≥3.5 |
| XuMLV | 0.14% | 3X | 30 | ≥3.5 |
| XuMLV | 0.14% | 3X | 60 | ≥3.5 |
| XuMLV | 0.14% | 3X | 120 | ≥4.6* |
| Run #2 | | | | |
| XuMLV | 0.14% | 3X | 5 | ≥3.3 |
| XuMLV | 0.14% | 3X | 15 | ≥3.3 |
| XuMLV | 0.14% | 3X | 30 | ≥3.3 |
| XuMLV | 0.14% | 3X | 60 | ≥3.3 |
| XuMLV | 0.14% | 3X | 120 | ≥4.4* |
| Run #3 | | | | |
| SuHV-1 | 0.14% | 3X | 5 | ≥3.2 |
| SuHV-1 | 0.14% | 3X | 15 | ≥3.2 |
| SuHV-1 | 0.14% | 3X | 30 | ≥3.2 |
| SuHV-1 | 0.14% | 3X | 60 | ≥3.2 |
| SuHV-1 | 0.14% | 3X | 120 | ≥4.2* |
| Run #4 | | | | |
| SuHV-1 | 0.14% | 3X | 5 | ≥2.3 |
| SuHV-1 | 0.14% | 3X | 15 | ≥2.3 |
| SuHV-1 | 0.14% | 3X | 30 | ≥2.3 |
| SuHV-1 | 0.14% | 3X | 60 | ≥2.3 |
| SuHV-1 | 0.14% | 3X | 120 | ≥3.4* |

Large volume sampling*.
Xenotrophic Murine Leukemia Virus = XuMLV
Suid Herpes-1 = SuHV-1.
Log reduction factor = LRF

EQUIVALENTS AND SCOPE

Those skilled in the art will recognize or be able to ascertain using no more than routine experimentation many equivalents to the specific embodiments described herein. The scope of the present invention is not intended to be limited to the above Description, but rather is as set forth in the appended claims.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, it is to be understood that the invention encompasses all variations, combinations, and permutations in which one or more limitations, elements, clauses, and descriptive terms, from one or more of the listed claims is introduced into another claim. For example, any claim that is dependent on another claim can be modified to include one or more limitations found in any other claim that is dependent on the same base claim.

Where elements are presented as lists, e.g., in Markush group format, it is to be understood that each subgroup of the elements is also disclosed, and any element(s) can be removed from the group. It should it be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not been specifically set forth in haec verba herein. It is also noted that the term "comprising" is intended to be open and permits the inclusion of additional elements or steps.

Where ranges are given, endpoints are included. Furthermore, it is to be understood that unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

The term "about" or "approximately" means within an acceptable error range for the particular value as determined by one of ordinary skill in the art, which will depend in part on how the value is measured or determined, e.g., the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, the term can mean within an order of magnitude, for example, within 5-fold, or within 2-fold, of a value. Where particular values are described in the application and claims, unless otherwise stated the term "about" meaning within an acceptable error range for the particular value should be assumed.

In addition, it is to be understood that any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the methods of the invention can be excluded from any one or more claims, for any reason, whether or not related to the existence of prior art.

Each of the foregoing patents, patent applications and references is hereby incorporated by reference, particularly for the teaching referenced herein.

What is claimed is:

1. A method of preparing a recombinant protein, the method comprising contacting a recombinant protein preparation with a zwitterionic detergent that is N,N-dimethyldodecylamine N-oxide (LDAO), N-dodecyl-N,N-dimethyl-3-ammonio-1-propanesulfonate (sulfobetaine 3-12), N-tetradecyl-N,N-dimethyl-3-ammonio-1-propanesulfonate (sulfobetaine 3-14), or N-hexadecyl-N,N-dimethyl-3-ammonio-1-propanesulfonate (sulfobetaine 3-16) in an amount sufficient to inactivate an enveloped virus that contaminates the recombinant protein preparation, wherein the amount is at a concentration above critical micelle concentration of the detergent and does not inhibit biological activity of the recombinant protein.

2. The method of claim 1, wherein the method further comprises culturing in cell culture media cells that express the recombinant protein.

3. The method of claim 1, wherein the method further comprises purifying the recombinant protein.

4. The method of claim 2, wherein the recombinant protein preparation is contacted with the zwitterionic detergent before, during, or after the culturing step.

5. The method of claim 3, wherein the recombinant protein preparation is contacted with the zwitterionic detergent during the purifying step.

6. The method of claim 1, wherein the concentration above the critical micelle concentration is about 2 times to about 10 times the critical micelle concentration.

7. The method of claim 1, wherein greater than about 4 log inactivation of the enveloped virus is achieved within 1 hour of contacting the zwitterionic detergent with the recombinant protein preparation.

8. The method of claim 1, wherein the recombinant protein is a tumor necrosis factor (TNF) inhibitor protein.

9. The method of claim 8, wherein the TNF inhibitor protein is etanercept.

10. The method of claim 1, wherein the enveloped virus is associated with a rodent cell line or a mammalian cell line.

11. The method of claim 10, wherein the enveloped virus is Xenotropic Murine Leukemia Virus or Suid Herpesvirus 1.

12. The method of claim 1, wherein the method does not comprise contacting the recombinant protein preparation with a solvent.

13. The method of claim 1, wherein the zwitterionic detergent is sulfobetaine 3-12.

14. The method of claim 1, wherein the zwitterionic detergent is sulfobetaine 3-14.

15. The method of claim 1, wherein the zwitterionic detergent is sulfobetaine 3-16.

\* \* \* \* \*